（12）United States Patent
Arakawa (10) Patent No.: US 11,051,679 B2
(45) Date of Patent: Jul. 6, 2021

(54) SUBSTRATE CONNECTION STRUCTURE AND ENDOSCOPE

(71) Applicant: Olympus Corporation, Hachioji (JP)

(72) Inventor: Naoki Arakawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 454 days.

(21) Appl. No.: 16/171,514

(22) Filed: Oct. 26, 2018

(65) Prior Publication Data

US 2019/0059704 A1 Feb. 28, 2019

Related U.S. Application Data

(63) Continuation of application No. PCT/JP2017/012616, filed on Mar. 28, 2017.

(30) Foreign Application Priority Data

Jun. 3, 2016 (JP) .............................. JP2016-112024

(51) Int. Cl.
*H05K 5/00* (2006.01)
*A61B 1/00* (2006.01)
(Continued)

(52) U.S. Cl.
CPC ........ *A61B 1/00124* (2013.01); *A61B 1/0008* (2013.01); *A61B 1/04* (2013.01);
(Continued)

(58) Field of Classification Search
CPC .. G06F 1/26; H05K 7/023; H01L 2924/01079
(Continued)

(56) References Cited

U.S. PATENT DOCUMENTS 5,032,088 A 7/1991 Kuramitsu
2012/0202385 A1 8/2012 Miyagi et al.
(Continued)

FOREIGN PATENT DOCUMENTS

JP 02-177277 7/1990
JP 04-088688 7/1992
(Continued)

OTHER PUBLICATIONS

Sep. 3, 2020 Office Action issued in Chinese Patent Application No. 201780034252.8.
(Continued)

*Primary Examiner* — Phuong Chi Thi Nguyen
(74) *Attorney, Agent, or Firm* — Oliff PLC (57) ABSTRACT

A substrate connection structure includes a tubular member, a first substrate, a second substrate, a first connector, a second connector, a first pin, and a guide member. The tubular member has a bottom portion and an opening side. The first substrate is disposed on either the bottom portion or the opening side. The second substrate is disposed on either the bottom portion or the opening side opposite to the first substrate. The first connector is disposed on the first substrate. The second connector is disposed on the second substrate and is connected to the first connector. The first pin is disposed on the first substrate. The first pin projects such as to extend from the first substrate along a direction of connection between the first connector and the second connector. The guide member is disposed on the second substrate. The guide member has a guide hole.

13 Claims, 10 Drawing Sheets

(51) Int. Cl.
- *H01R 12/70* (2011.01)
- *H01R 13/645* (2006.01)
- *A61B 1/04* (2006.01)
- *A61B 1/06* (2006.01)
- *G02B 23/24* (2006.01)

(52) U.S. Cl.
CPC ........ *A61B 1/0661* (2013.01); *G02B 23/2476* (2013.01); *H01R 12/70* (2013.01); *H01R 13/6456* (2013.01); *A61B 1/00126* (2013.01); *A61B 1/00128* (2013.01); *H01R 2201/00* (2013.01)

(58) Field of Classification Search
USPC .......................................... 361/730, 735, 760
See application file for complete search history.

(56) References Cited

U.S. PATENT DOCUMENTS

| | | | | |
|---|---|---|---|---|
| 2014/0094067 A1* | 4/2014 | Kubo | ................... | H01R 13/46 439/660 |
| 2014/0187060 A1* | 7/2014 | Kubo | ................... | H01R 13/58 439/65 |
| 2014/0202628 A1* | 7/2014 | Sreetharan | .......... | B32B 37/0076 156/257 |
| 2015/0176817 A1* | 6/2015 | Olsson | ................... | F21V 29/83 362/249.02 |
| 2019/0324496 A1* | 10/2019 | Cherukkate | .............. | H04R 1/08 |

FOREIGN PATENT DOCUMENTS

| | | |
|---|---|---|
| JP | 2506608 | 5/1996 |
| JP | 08-213104 | 8/1996 |
| JP | 4960533 | 3/2012 |
| JP | 2016-043021 | 4/2016 |
| WO | 2011052408 | 5/2011 |

OTHER PUBLICATIONS

International Search Report and Written Opinion from corresponding International Application No. PCT/JP2017/012616, dated May 9, 2017.

Office Action from corresponding Japanese Application No. 2017535477, dated Sep. 6, 2017.

* cited by examiner

SUBSTRATE CONNECTION STRUCTURE AND ENDOSCOPE

CROSS-REFERENCE TO RELATED APPLICATIONS

This application is a continuation application of PCT Application No. PCT/JP2017/012616 filed on Mar. 28, 2017, which in turn claim priority to the Japanese Patent Application No. 2016-112024 filed on Jun. 3, 2016 in Japan which is hereby incorporated by reference in its entirety.

TECHNICAL FIELD

The technology disclosed herein generally relates to a substrate connection structure for electrically connecting two substrates to each other, and an endoscope having the connection structure.

DESCRIPTION OF THE RELATED ART

US 2012/0202385 A1 discloses an endoscope having a connection portion for connecting with an external apparatus (light source) that includes a cylindrical exterior part (armor or sheath). Two substrates are disposed inside of the exterior part of the connection portion. Each of the substrates includes an electric circuit and a connector. The connectors that disposed on the substrates are connected to each other, whereby the substrates are electrically connected to each other. Japanese Patent No. 4960533 disclose a connection structure between substrates.

BRIEF SUMMARY OF EMBODIMENTS

One aspect of the technology disclosed herein is directed to a substrate connection structure. The substrate connection structure includes a tubular member, a first substrate, a second substrate, a first connector, a second connector, a first pin, and a guide member. The tubular member has a bottom portion and an opening side. The first substrate is disposed on either the bottom portion or the opening side in an inside of the tubular member. The second substrate is disposed on either the bottom portion or the opening side opposite to the first substrate in the inside of the tubular member. The first connector is disposed on the first substrate. The second connector is disposed on the second substrate and is connected to the first connector. The first pin is disposed on the first substrate. The first pin projects such as to extend from the first substrate along a direction of connection between the first connector and the second connector. The guide member is disposed on the second substrate. The guide member has a guide hole in which the first pin is fitted. An angle generated between the first pin and the guide hole due to a fitting gap between the first pin and the guide hole when the first pin and the guide hole are fitted to each other is so set as to be not greater than an allowable angle in connection between the first connector and the second connector.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

In a connection structure between substrates, one of the connected substrates may be inclined relative to the other. In this instance, the angle between the connectors connected to each other may exceed an allowable angle necessary for maintaining the connection between the connectors. When the angle between the connectors exceeds the allowable angle, the electrical connection between the substrates may not be maintained. The present disclosure has been made for solving the above-mentioned problem. It is an object of the present disclosure to provide a substrate connection structure and an endoscope having the connection structure. The angle between connectors connected to each other can be prevented from exceeding an allowable angle by the substrate connection structure.

In order to achieve the above object, according to an aspect of the present disclosure, a substrate connection structure includes a first substrate, a second substrate, a first connector, a second connector, a pin, and a guide member. The first connector is disposed on the first substrate. The second connector is disposed on the second substrate and is connected to the first connector. The pin is disposed on the first substrate. The pin projects such as to extent from the first substrate along the direction of connection between the first connector and the second connector. The guide member is disposed on the second substrate. The guide member has a guide hole in which the pin is fitted. An angle is generated between the pin and the guide hole based on a fitting gap between the pin and the guide hole when the pin and the guide hole are fitted to each other. The angle is so set as to be not greater than an allowable angle in connection between the first connector and the second connector.

Figure 1:
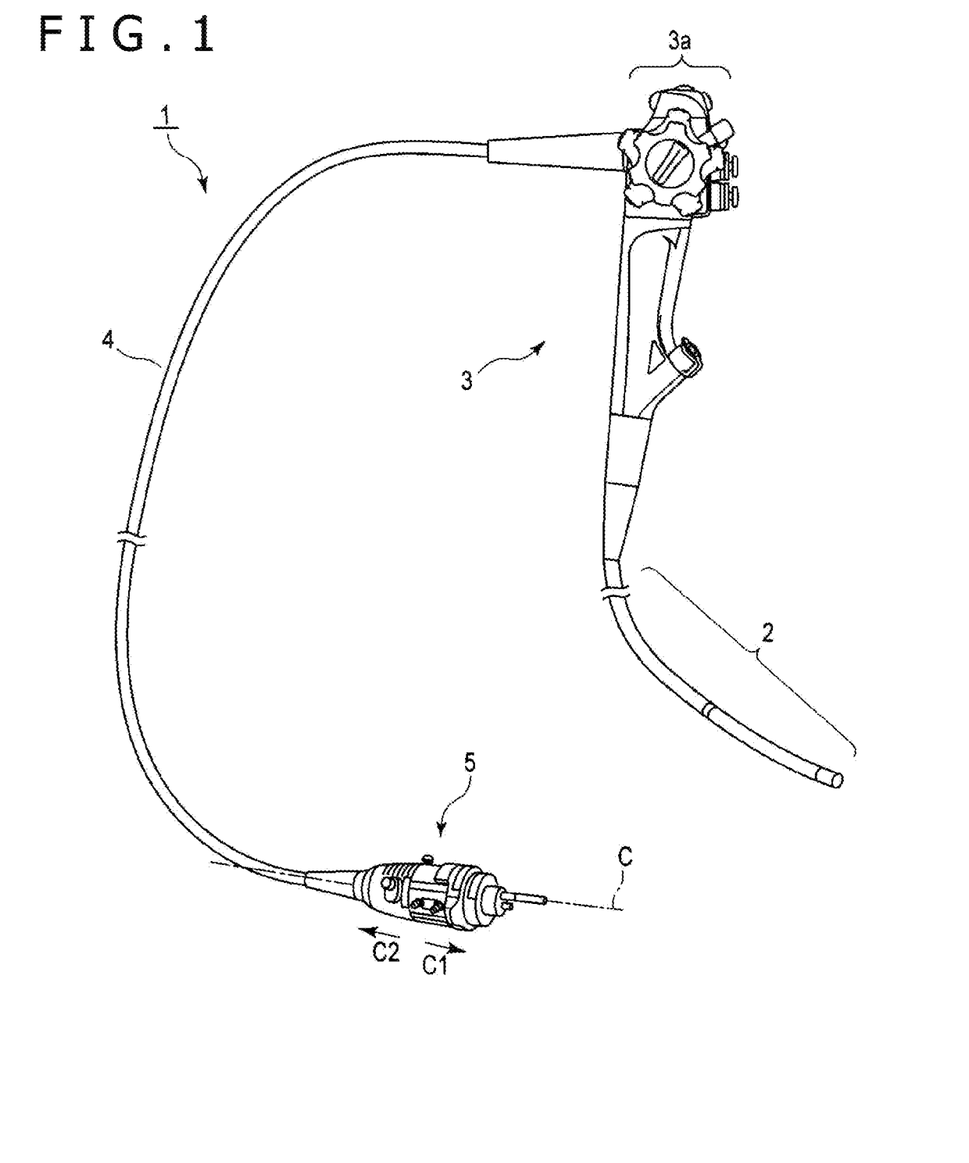
FIG. 1 is a perspective view depicting an endoscope according to an embodiment.

An embodiment of the present disclosure will be described referring to FIGS. 1 to 10. FIG. 1 is a figure depicting an endoscope which is an insertion apparatus. As depicted in FIG. 1, the endoscope 1 includes an insertion portion 2 to be inserted to an object site to be observed, such as for example a lumen. An operation portion 3 is connected to the insertion portion 2. A universal cable 4 is extended from a side surface of the operation portion 3. A connection portion 5 is disposed at an end portion of the universal cable 4. An illumination optical system and an observation optical system, and, further, a plurality of tubes for suction, gas feed, water feed and the like are incorporated in the connection portion 5, the universal cable 4, the operation portion 3 and the insertion portion 2. The connection portion 5 is detachably connected to an external apparatus (not depicted) including a light source device, a processor and the like. Therefore, the endoscope 1 and the external apparatus are electrically connected through the connection portion 5. Besides, electric power is supplied from the external apparatus to the endoscope 1, and/or electrical signals are transmitted between the external apparatus and the endoscope 1.

Note that the operation portion 3 has various switches 3*a* for appropriately operating the observation optical system. Since the endoscope 1 and the external apparatus are electrically connected, the observation optical system can be appropriately controlled by operating one of the switches 3*a*. In addition, it is also preferable that the endoscope 1 and the external apparatus are optically connected through the connection portion 5. A longitudinal axis C is defined in the connection portion 5. Here, a direction along (substantially parallel to) the longitudinal axis C is a longitudinal direction. Besides, one side in regard of the longitudinal direction is a distal side (arrow C1 side), and the side opposite to the distal side is a proximal side (arrow C2 side).

Figure 2:
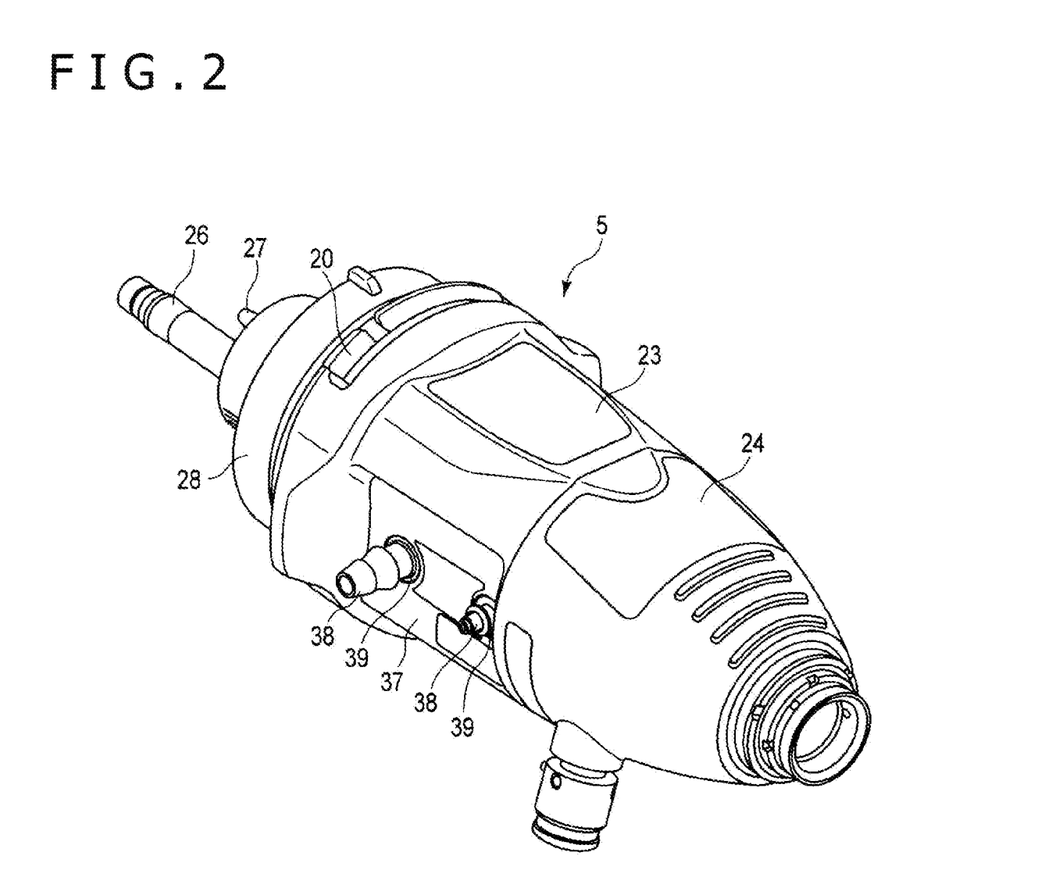
FIG. 2 is a perspective view of a portion of endoscope in FIG. 1 depicting a connector according to the embodiment.

FIG. 2 is a perspective view of a portion of endoscope in FIG. 1 depicting a connector according to the embodiment. A connection member 28 is disposed at a distal portion of the connection portion 5. The connection member 28 is connected to an external apparatus. The connection member 28 is formed by at least one contact pin 31, and an insulating material that covers part of the contact pin 31 (see FIG. 3). On the proximal side of the connection member 28, a substantially cylindrical connector case 23 is extended along the longitudinal direction. Between the connection member 28 and the connector case 23, is interposed a substantially disk-shaped metallic frame (base) 20. On the proximal side of the connector case 23, a pipe-shaped connector cover 24 is attached. The connector cover 24 is extended along the longitudinal direction C. The connector cover 24 becomes smaller in diameter in going toward the proximal side. A distal end (a distal end in relation to the operation portion 3) of the universal cable 4 is connected to a proximal portion of the connector cover 24.

A light guide port 26 and a gas feed port 27 are disposed at a distal end surface of the connection member 28. In the light guide port 26, light is supplied from an external apparatus (light source). The light is applied to the object to be observed at the insertion portion 2. In addition, in the gas feed port 27, a gas is fed at the insertion portion 2 is supplied from an external apparatus. While an example in which the light guide port 26 is disposed at the distal end surface of the connection member 28 is described herein, the light guide port 26 is unnecessary in the case where the illumination optical system has a light emitting element such as an LED in the endoscope 1.

As depicted in FIG. 2, the connector case 23 has a port disposing portion 37. The port disposing portion 37 is formed with at least one port projection portion 39 that penetrates the connector case 23. A port 38 is disposed in the inside of the connection portion 5. At the port disposing portion 37, the port 38 projects from the respective one of the port projection portion 39 toward the outside of the connector case 23. The port 38 is used, for example, for a water feed port, or a pressure pipe port, or a suction port or the like.

Figure 3:
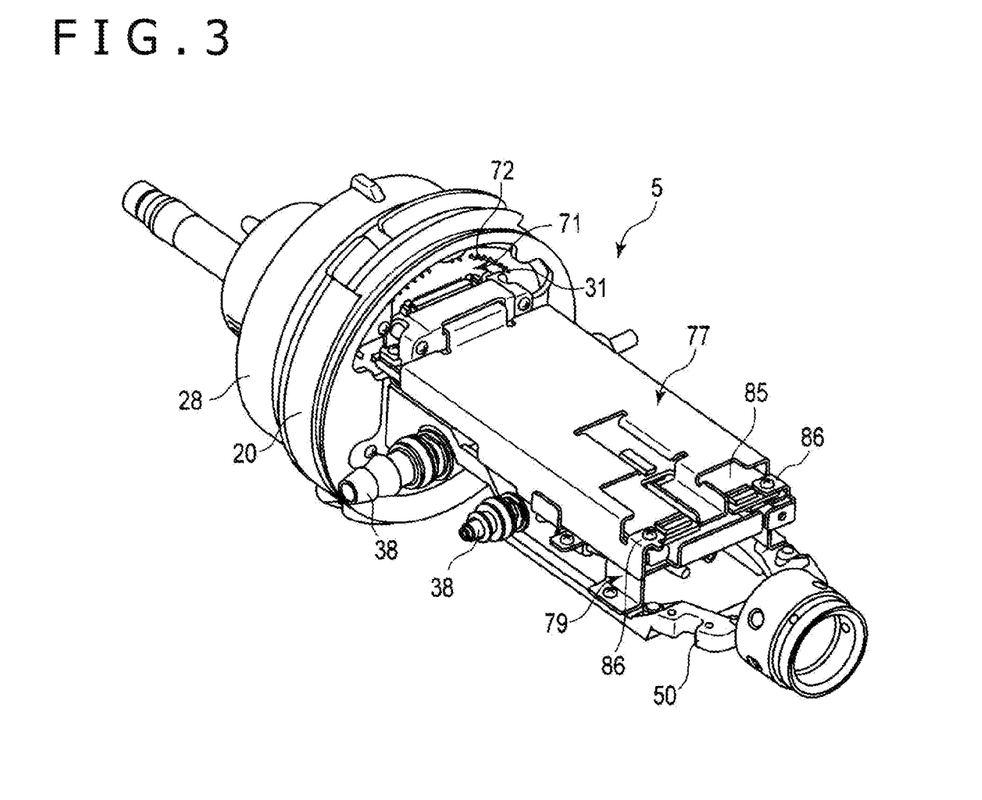
FIG. 3 is a perspective view of the connector in FIG. 2 depicting the configuration of the inside of the connector according to the embodiment.

FIG. 3 is a figure depicting a state in which the connector case 23 and the connector cover 24 in the connection portion 5 are detached. As depicted in FIG. 3, the port 38 is disposed inside the connection portion 5. The port 38 projects from the inside of the connection portion 5 to the exterior of the connection portion 5 through the port projection portion 39 disposed at the port disposing portion 37 of the connector case 23. Between the connection member 28 and the metallic frame 20, a first substrate 71 is disposed substantially perpendicularly to the longitudinal direction. The first substrate 71 is a substantially disk-shaped electric substrate. An electric circuit is formed on a surface of the first substrate 71. The first substrate 71 is formed with a plurality of through-hole 72 arranged in an arcuate pattern along a peripheral edge. In each of the through-hole 72, an end portion of the contact pin 31 is inserted. The contact pin 31 extends from the connection member 28 toward the proximal side. With this configuration, the connection member 28 and the first substrate 71 are electrically connected to each other.

A main frame 50 is attached to the metallic frame 20 by small screws or the like (not depicted). The main frame 50 is a plate-shaped member extended along the longitudinal direction. The main frame 50 is formed from a metallic material such as a stainless steel material, for example. A distal portion of a shield case 77 is extended along the longitudinal direction and is connected to a surface on the proximal side of the first substrate 71. The shield case 77 is disposed substantially in parallel to the main frame 50. The shield case 77 is formed from a metallic material. A second substrate 85 is in plate-shape and is disposed inside the shield case 77. The second substrate 85 is disposed substantially in parallel to the shield case 77, and is screwed to the shield case 77 at a plurality of attachment portions 86. An electric circuit is formed on a surface of the second substrate 85. The second substrate 85 is electrically connected to the switch 3*a* at the operation portion 3 through a connection cable or the like (not depicted). The second substrate 85 is connected to a first connector 60, which will be described hereinafter, of the first substrate 71 through a second connector 80 described hereinafter. The first substrate 71 and the second substrate 85 are connected substantially orthogonally to each other. Thus, the second substrate 85 and the first substrate 71 are electrically connected to each other. A connection structure between the first substrate 71 and the second substrate 85 will be described hereinafter. Here, the first substrate 71 is electrically connected to an external apparatus through the connection member 28. Therefore, the endoscope 1 (for example, the switch 3a at the operation portion 3) and the external apparatus are electrically connected to each other through the electrical connection between the second substrate 85 and the first substrate 71.

Figure 4:
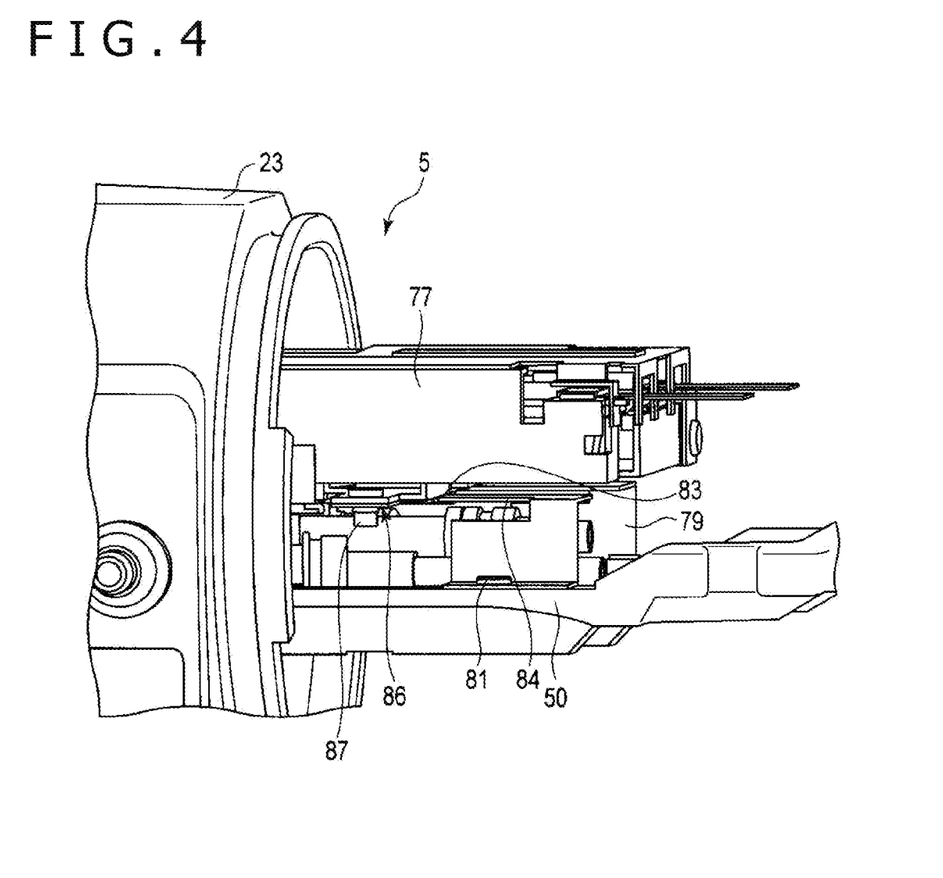
FIG. 4 is a perspective view of the connector in FIG. 3 depicting a substrate base attached to a main frame according to the embodiment.

Between the shield case 77 and the main frame 50, is disposed a substrate base 79, which is a plate-shaped metallic member. The substrate base 79 is disposed substantially in parallel to the shield case 77 and the main frame 50. FIG. 4 is a figure depicting the shield case 77, the main frame 50 and the substrate base 79. As depicted in FIG. 4, the substrate base 79 has a contact surface 83 that makes contact with one surface of the shield case 77. The substrate base 79 is screwed to the main frame 50 at an attachment portion 81. At the contact surface 83 of the substrate base 79, there is an attachment portion 86. The substrate base 79 is detachably attached, at the attachment portion 86, to the shield case 77. At the attachment portion 86, the shield case 77 and the substrate base 79 are formed with engagement holes (not depicted). With a screw 87 inserted in these engagement holes, the substrate base 79 is attached to the shield case 77.

Depending on variability in sizes of component parts, a mis-alignment as to the attachment position between the shield case 77 and the substrate base 79 may be generated. In the present embodiment, even in such a case, the engagement hole in the shield case 77 is formed to be larger in diameter than the screw 87. In this structure, the shield case 77 can be appropriately attached to the substrate base 79 even if there is a certain degree of mis-alignment as to the position of the shield case 77 relative to the substrate base 79 in a direction along the contact surface 83. In addition, the substrate base 79 includes, between the first attachment portion 81 and the second attachment portion 86, a leaf spring portion 84 having a leaf spring structure. By the leaf spring portion 84, a mis-alignment in a direction substantially perpendicular to the contact surface 83 can be absorbed. Therefore, even in the case where mis-alignment as to the attachment position of the shield case 77 is generated in the direction substantially perpendicular to the contact surface 83 due to variability in the sizes of component parts, the shield case 77 can be attached with the mis-alignment as to the attachment position, by elastic variation of the position of the contact surface 83.

Figure 5:
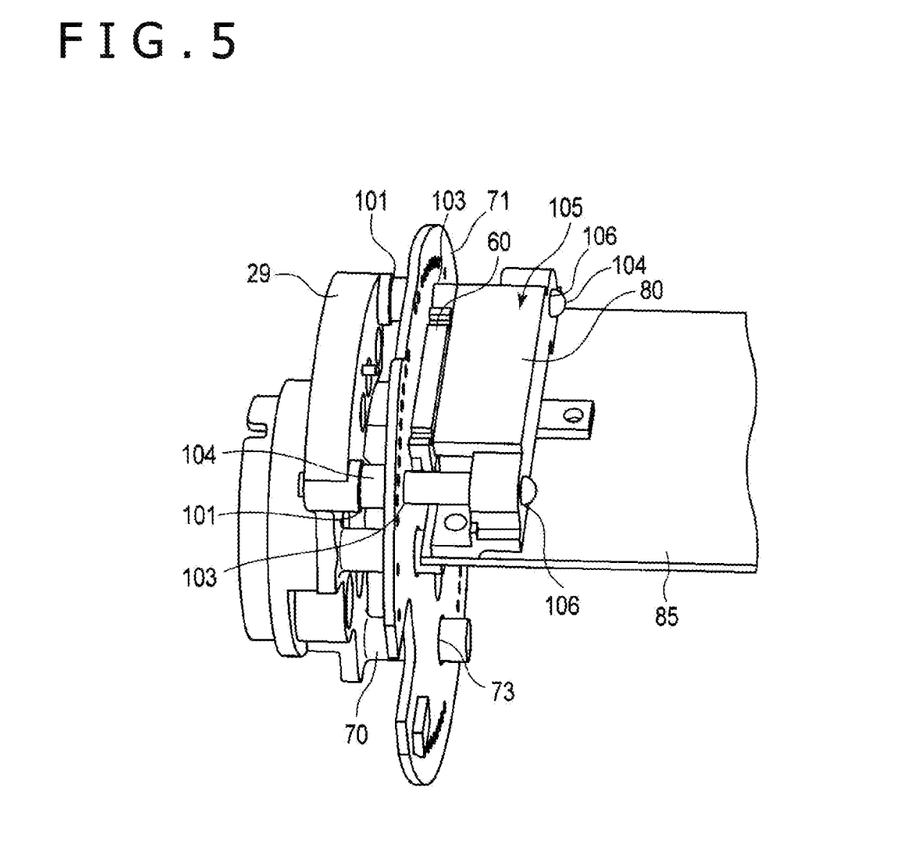
FIG. 5 is a perspective view depicting a connection structure between a first substrate and a second substrate according to the embodiment.

FIG. 5 is a figure depicting a connection structure between the first substrate 71 and the second substrate 85. An attachment member 29 is attached on the inner surface side of the connection member 28. As depicted in FIG. 5, an attachment member 29 is disposed with a plurality of holes 101 extended along the longitudinal direction. The first substrate 71 is disposed on the proximal side of the attachment member 29. Here, the first substrate 71 is formed with a plurality of holes 73. While the holes 73 are described here to be disposed in plurality, only one hole 73 may be disposed. A pin 70 is extended from the attachment member 29 in the longitudinal direction and is inserted in the hole 73. The pin 70 is fitted in the hole 101 in the attachment member 29 in the state of being fitted in the hole 73. The number of the pins 70 is preferably equal to or smaller than the number of holes 73. Only one pin 70 may be disposed, or a plurality of pins 70, for example, two pins 70 may be disposed. Besides, the pin 70 may be formed to be integral with the attachment member 29.

The first substrate 71 is disposed with the first connector 60 projecting from the first substrate 71 toward the proximal side. The first connector 60 is formed in a substantially rectangular parallelepiped external shape. The first connector 60 is preferably erected perpendicularly to the first substrate 71. The first substrate 71 is disposed with holes 103 on both sides of the first connector 60. The holes 103 penetrates the first substrate 71 in the longitudinal direction. Guide pins 104 in a substantially cylindrical shape are fitted respectively in the holes 101 in the attachment member 29. In other words, base portions of the guide pins 104 are attached to the attachment member 29. Each of the guide pins 104 projects toward the proximal side through the hole 103 in the first substrate 71. By this, the position of the first substrate 71 relative to the attachment member 29 is determined. In other words, the two guide pins 104 are disposed at such positions that the first connector 60 is interposed therebetween.

A guide member 105 is disposed at a distal portion of the second substrate 85. The guide member 105 is screwed to the second substrate 85. The guide member 105 is disposed with the second connector 80. The second connector 80 is formed in a substantially rectangular parallelepiped external shape. The first connector 60 disposed on the first substrate 71 is fitted to the second connector 80. With the first connector 60 and the second connector 80 fitted to each other, the first substrate 71 and the second substrate 85 are electrically connected to each other.

Note that in FIGS. 7A to 8B, there is depicted an example in which the first connector 60 is formed as a male-type connector while the second connector 80 is formed as a female-type connector. The first connector 60 may be of a female type, and the second connector 80 may be of a male type. The guide member 105 can cover and protect the second connector 80. The guide member 105 is disposed with guide holes 106 on both sides of the second connector 80 in regard of the width direction of the second substrate 85 (the direction substantially perpendicular to the longitudinal direction of the second substrate 85). The guide member 105 and the guide holes 106 are preferably formed integrally. The guide holes 106 are through-holes that penetrate the guide member 105 in the longitudinal direction. Guide pins 104 projects from the first substrate 71 toward the proximal side. The guide pins 104 are inserted in the guide holes 106 from the distal side of the guide holes 106. In other words, the guide pins 104 are projections that project from the first substrate 71 along the direction in which the first connector 60 and the second connector 80 are connected together.

Figure 6:
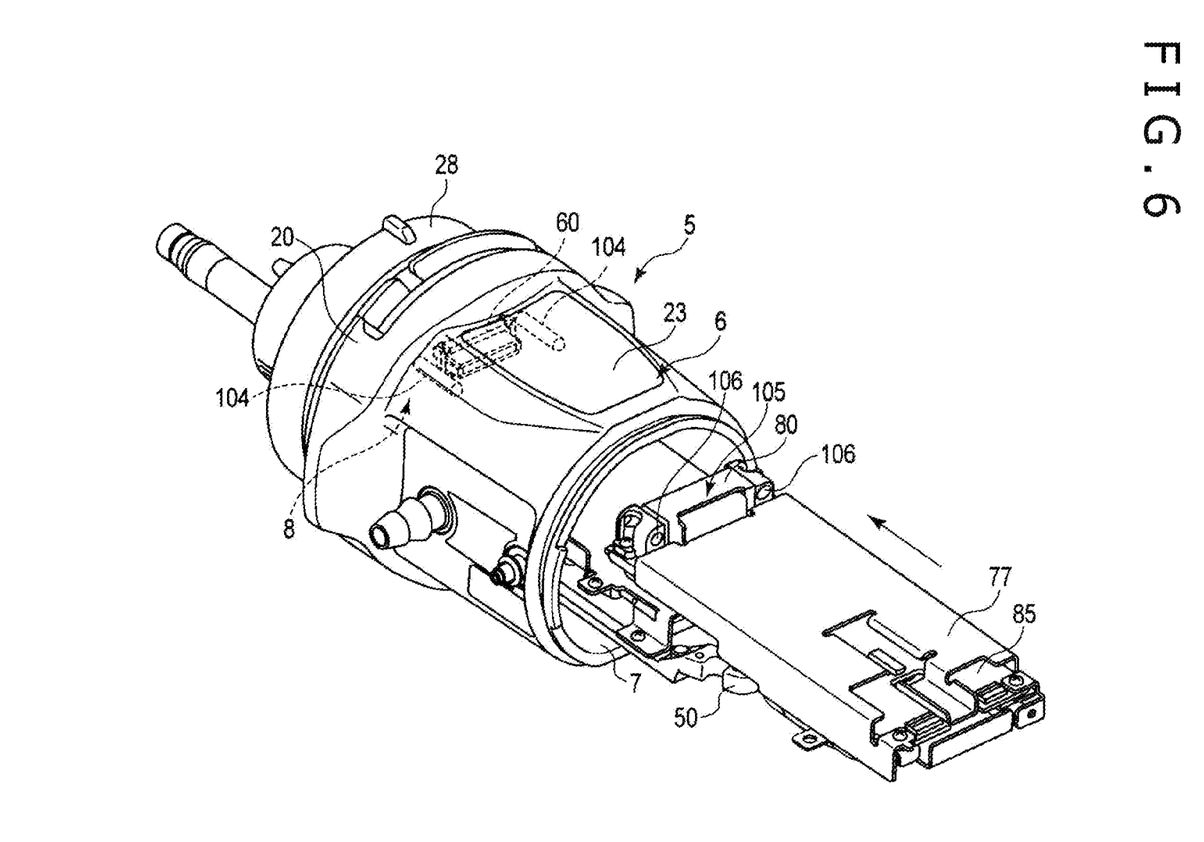
FIG. 6 is a perspective view depicting the manner in which the first substrate and the second substrate are connected.

An operation and effect of the present embodiment will be described hereinafter, referring to FIGS. 6 to 10. FIG. 6 is a view depicting the manner in which the first substrate 71 and the second substrate 85 are connected to each other at the time of manufacturing the connection portion 5. As depicted in FIG. 6, at the time of manufacturing the connection portion 5, the first substrate 71, the metallic frame 20 and the connector case 23 are mounted to the connection member 28. The main frame 50 is attached to the metallic frame 20. In this instance, the connection member 28, the metallic frame 20 and the connector case 23 form an exterior part 6 of the connection portion 5. The exterior part 6 is a tubular member that has a bottom portion 8 at a distal portion (one end) thereof and has an opening 7 at a proximal portion (the other end) thereof. In other words, the exterior part 6 is a tubular member formed to have a bottom. A state is established in which the first substrate 71 is disposed at the bottom portion 8 or in the vicinity of the bottom portion 8, in the inside of the exterior part 6. In this state, the shield case 77 is inserted along one surface of the main frame 50, from the opening 7 toward the bottom portion 8 (see arrow in FIG. 6). The second substrate 85 is attached inside the shield case 77, and the second connector 80 is disposed at a distal portion of the second substrate 85. With the shield case 77 inserted into the inside of the exterior part 6, the second connector 80 and the first connector 60 disposed on the first substrate 71 are connected to each other, and the first substrate 71 and the second substrate 85 are electrically connected to each other.

The first connector 60 and the second connector 80 are connected to each other at the bottom portion 8 of the exterior part 6. In this instance, the connection part between the first connector 60 and the second connector 80 is connected in a state in which the connector case 23 is mounted to the proximal side of the connection member 28. Therefore, the connection part is difficulty visible from the exterior (opening 7). Accordingly, it is difficult for an assembling worker to appropriately connect the first connector 60 and the second connector 80. In the case where the first connector 60 and the second connector 80 are not appropriately connected together, the first connector 60 and the second connector 80 may contact each other at an inappropriate angle, and a load may be exerted on the first connector 60 and the second connector 80.

In addition, for the first connector 60 and the second connector 80, an introduction range (introduction error) for connection of the second connector 80 to the first connector 60 is set. The introduction range is determined according to the structure, physical properties, electrical properties and the like of the first connector 60 and the second connector 80. Assume the first case where a mis-alignment between the first connection 60 and the second connection 80 is not greater than the introduction range, with respect to a plane intersecting the direction of connection between the first connector 60 and the second connector 80. In the first case, the second connector 80 is appropriately connected to the first connector 60. Assume the second case where the mis-alignment between the first connector 60 and the second connector 80 is greater than the introduction range. In the second case, the first connector 60 and/or the second connector 80 may contact other component parts than them.

Figure 7A:
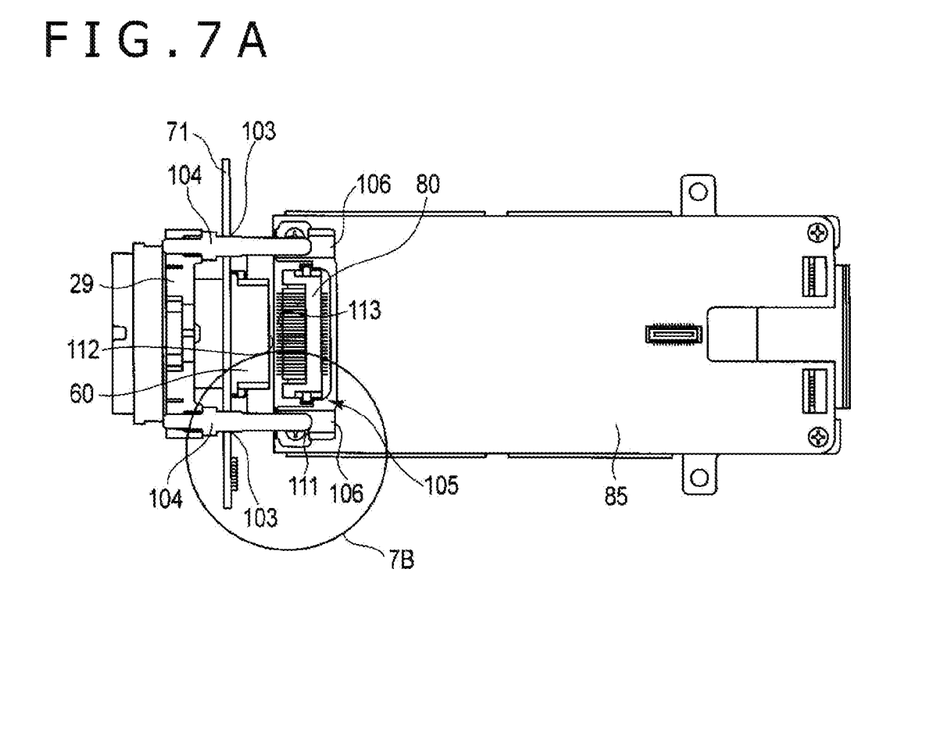
FIG. 7A is a view depicting the manner in which a proximal end of a guide pin faces and is fitted to a distal end of a guide hole.
Figure 8A:
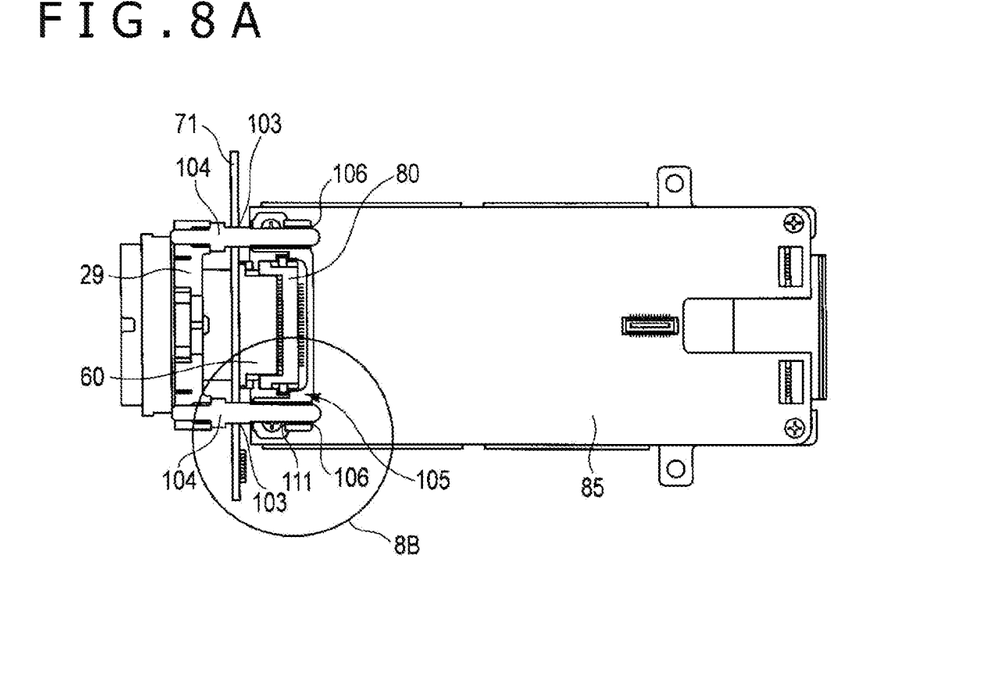
FIG. 8A is a view depicting a state in which the guide pin according to the embodiment is fitted in the guide hole.

FIG. 7A is a view depicting a state immediately before insertion of the guide pins 104 into the guide holes 106, at the time of connection between the first substrate 71 and the second substrate 85, according to the present embodiment. In addition, FIG. 8A is a figure depicting a state in which the guide pin 104 is connected to the guide hole 106. As depicted in FIG. 7A, of the first connector 60, a first facing surface 112 oriented to the proximal side faces the second connector 80. In addition, of the second connector 80, a second facing surface 113 oriented toward the distal side faces the first connector 60. The guide hole 106 is disposed on the proximal side relative to the second facing surface 113 of the second connector 80. In other words, a fitting part 111 of the guide hole 106 for fitting to the guide pin 104 is disposed on the side opposite to the first substrate 71 (the proximal side), as compared to that surface (second facing surface 113) of the second connector 80 which faces the first substrate 71.

Figure 7B:
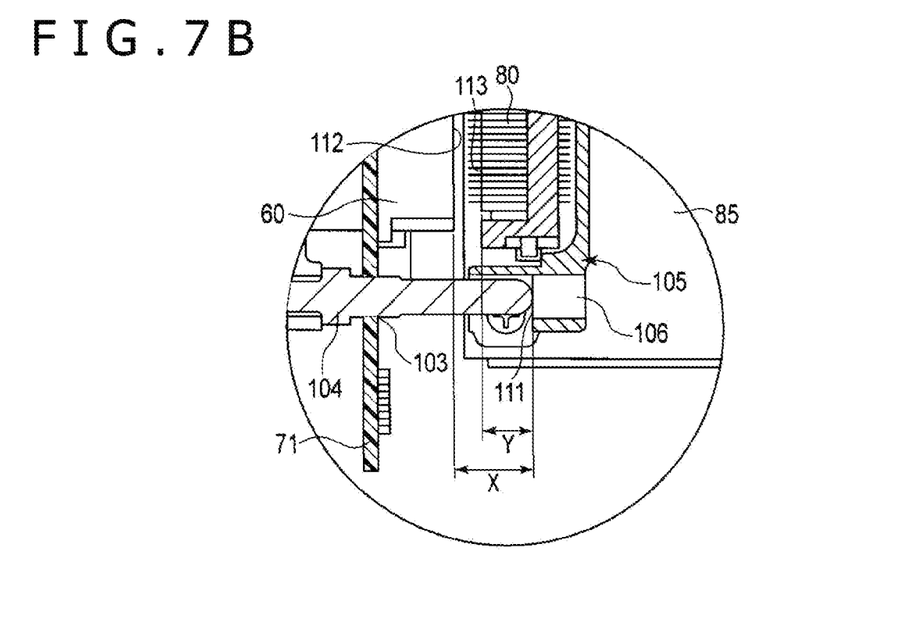
FIG. 7B is an enlarged form, the part indicated by reference symbol 7B of FIG. 7A.

FIG. 7B is a view depicting, in an enlarged form, the connection part between the guide pin 104 and the guide hole 106, in FIG. 7A. The guide pin 104 protrudes to the proximal side beyond the proximal end of the first connector 60. The fitting part 111 of the guide hole 106 fits to the guide pin 104. As depicted in FIG. 7B, "X" is described as the size of that part of the guide pin 104 which protrudes to the proximal side beyond the proximal end of the first connector 60, in the protruding direction. In addition, "Y" is described as the distance between the distal end of the second connector 80 and the fitting part 111 in the extending direction of the second substrate 85. In the present embodiment, the shapes and sizes and the like of members are determined such that X>Y. In other words, the size (X) of that part of the guide pin 104 which protrudes to the proximal side beyond the proximal end of the first connector 60, in the protruding direction, is greater than the distance (Y) between the distal end of the second connector 80 and the distal end of the guide hole 106, in the extending direction of the second substrate 85, in the guide member 105.

As seen from FIGS. 7A and 7B, at the time point immediately before insertion of the guide pin 104 into the guide hole 106, the distance between the first facing surface 112 and the second facing surface 113 is (X−Y). Here, as aforementioned, X>Y. Therefore, X−Y>0. Accordingly, at the time point immediately before the insertion of the guide pin 104 into the guide hole 106, a distance is present between the first facing surface 112 and the second facing surface 113, and the first connector 60 and the second connector 80 are not yet connected to each other. In other words, the guide pin 104 starts being guided by the guide hole 106 before the first connector 60 and the second connector 80 are connected to each other. Then, the second substrate 85 is moved toward the first substrate 71, and the guide pin 104 and the guide hole 106 are slid mutually. Then, the first connector 60 and the second connector 80 are attached together (see FIGS. 8A and 8B). Therefore, after the connection, the insertion length of the guide pin 104 from the fitting part 111 of the guide hole 106 (the length from the fitting part 111 to the distal end, of the guide pin 104) is greater than the distance from the first facing surface 112 to the second facing surface 113, or the fitting length of the first connector 60 and the second connector 80.

Figure 8B:
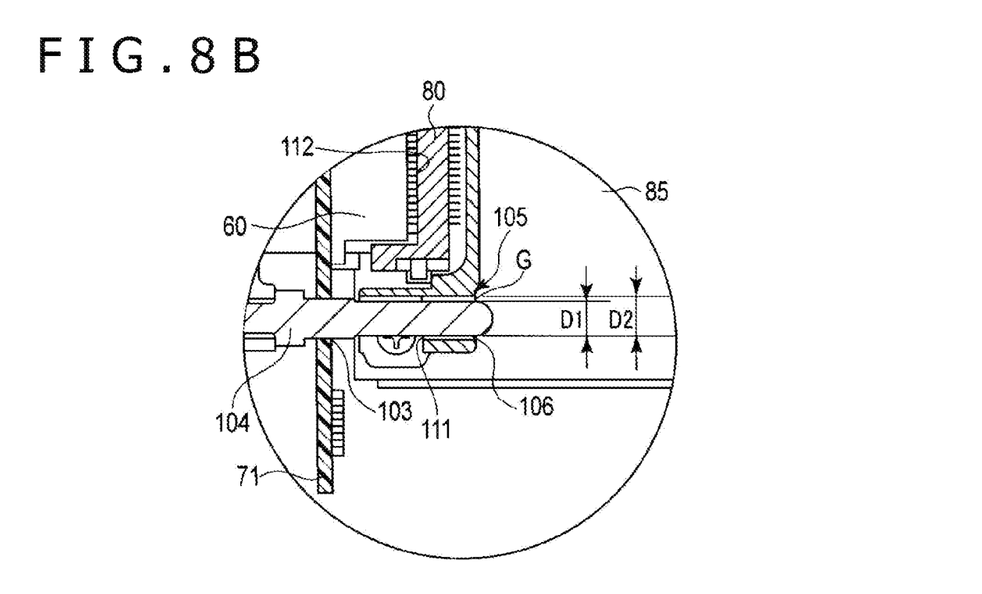
FIG. 8B is an enlarged form, the part indicated by reference symbol 8B of FIG. 8A.

FIG. 8B is a figure depicting, in an enlarged form, the connection part between the guide pin 104 and the guide hole 106, in FIG. 8A. As depicted in FIG. 8B, the diameter length (diameter) of the guide pin 104 is D1, and the diameter length (diameter) of the guide hole 106 is D2. In addition, a gap generated between the guide hole 106 and the guide pin 104 is a fitting gap G. In this instance, the fitting gap G is (D2−D1) at maximum. Therefore, the mis-alignment between the second connector 80 and the first connector 60 is the maximum size (D2−D1) of the fitting gap G, at maximum. In the present embodiment, the diameter length D2 of the guide hole 106 and the diameter length D1 of the guide pin 104 are so set that the maximum (D2−D1) of the fitting gap G is smaller than the introduction range. Therefore, the mis-alignment between the second connector 80 and the first connector 60 is smaller than the introduction range.

In the present embodiment, the first connector 60 and the second connector 80 start being connected to each other after the guide pin 104 starts being guided by the guide hole 106. In addition, the fitting gap generated between the guide hole 106 and the guide pin 104 is adjusted to be smaller than the introduction range. Therefore, the mis-alignment between the second connector 80 and the first connector 60 is smaller than the introduction range. For this reason, the first connector 60 and the second connector 80 are appropriately connected together within the scope of the introduction range.

Figure 9:
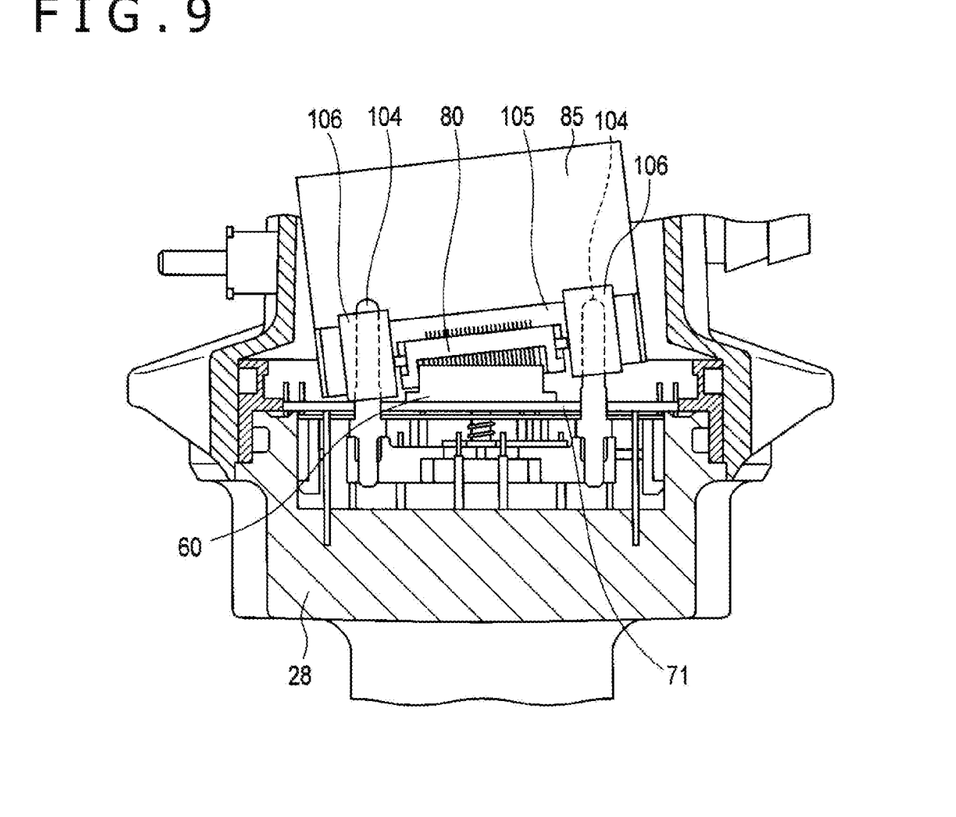
FIG. 9 is a view depicting a state in which the second substrate is inclined relative to the first substrate.

In addition, if the attachment at the screw attachment portion 81 is spoiled during repeated use of the endoscope 1 or the like, the shield case 77 and the second substrate 85 inserted in the connection portion 5 may be inclined relative to the first substrate 71. FIG. 9 is a figure depicting the manner in which the second substrate 85 is inclined relative to the first substrate 71. As depicted in FIG. 9, when the second substrate 85 is inclined relative to the first substrate 71, the second connector 80 of the second substrate 85 is inclined relative to the first connector 60 of the first substrate 71 in the state of being connected with the first connector 60. Here, an allowable angle θ for maintaining the state of connection of the second connector 80 to the first connector 60 is set for the first connector 60 and the second connector 80. The allowable angle θ is determined according to the physical properties, shapes or the like of the first connector 60 and the second connector 80. Here, in the case where the inclination, or angle, of the second connector 80 relative to the first connector 60 is not greater than the allowable angle θ, electrical connection between the first connector 60 and the second connector 80 is maintained appropriately. In the case where the inclination, or angle, of the second connector 80 relative to the first connector 60 is greater than the allowable angle θ, a load is exerted on the first connector 60 and the second connector 80, so that the electrical connection between the first connector 60 and the second connector 80 may not be maintained appropriately.

Figure 10:
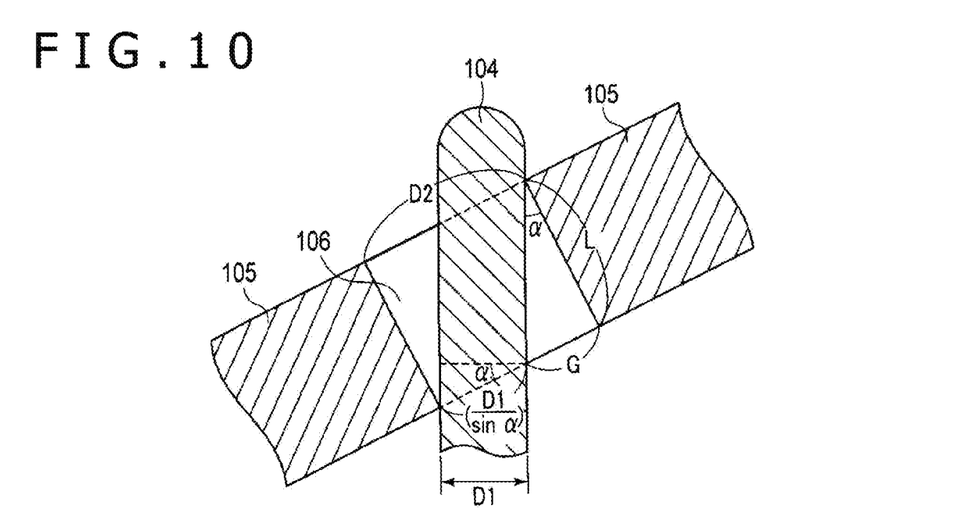
FIG. 10 is a view depicting a connection structure between the guide pin and the guide hole, in a state in which the second substrate is inclined most relative to the first substrate.

In the present embodiment, in addition to the connection part between the first connector 60 and the second connector 80, a connection part is formed by insertion of the guide pin 104 into the guide hole 106. By the connection part between the guide pin 104 and the guide hole 106, the guide hole 106 is restricted from being inclined more largely than a predetermined angle in relation to the guide pin 104. FIG. 10 is a figure depicting the connection part between the guide hole 106 and the guide pin 104 in a state in which the guide hole 106 is inclined most relative to the guide pin 104. As depicted in FIG. 10, the diameter length (diameter) of the guide pin 104 is D1, the diameter length of the guide hole 106 is D2, the length in the longitudinal direction of the guide hole 106 is L, and the inclination, or angle, of the guide hole 106 relative to the guide pin 104 is α. When the guide pin 104 penetrates and is fitted to the guide hole 106, the length L in the longitudinal direction of the guide hole 106 is the fitting length of the guide hole 106 and the guide pin 104. In addition, the fitting gap G formed between the guide hole 106 and the guide pin 104 at the fitting part 111 between the guide pin 104 and the guide hole 106 is represented by the following formula (1).

$$G = D2 - (D1/\cos \alpha) \quad (1)$$

Besides, the relation between the angle α in the state in which the guide hole 106 is inclined most relative to the guide pin 104 and the sizes (D1, D2, L) concerning the guide pin 104 and the guide hole 106 is represented by the following formula (2).

$$\tan \alpha = G/L = (D2 - (D1/\cos \alpha))/L \quad (2)$$

By use of the formula (2), the inclination α in the state in which the guide hole 106 is inclined most relative to the guide pin 104 is calculated from the sizes (D1, D2, L) concerning the guide pin 104 and the guide hole 106. In the present embodiment, the sizes (D1, D2, L) concerning the guide pin 104 and the guide hole 106 are adjusted in such a manner that the inclination α in the state in which the guide hole 106 is most inclined relative to the guide pin 104 is not greater than the allowable angle θ. In other words, the sizes (D1, D2, L) concerning the guide pin 104 and the guide hole 106 are adjusted such that the following formula (3) is satisfied.

$$\tan \alpha = G/L \leq \tan \theta \quad (3)$$

As a result of this, the inclination α of the guide hole 106 relative to the guide pin 104 is always maintained in the state of being not greater than the allowable angle θ. In other words, the guide hole 106 is restricted from being inclined more largely than the allowable angle θ in relation to the guide pin 104. With the guide hole 106 restricted from being inclined more largely than the allowable angle θ in relation to the guide pin 104, the second substrate 85 is restricted from being inclined more largely than the allowable angle θ in relation to the first substrate 71. Besides, with the second substrate 85 restricted from being inclined more largely than the allowable angle θ in relation to the first substrate 71, the second connector 80 is restricted from being inclined more largely than the allowable angle θ in relation to the first connector 60. Thus, by adjustment of the sizes (D1, D2, L) concerning the guide pin 104 and the guide hole 106, the second connector 80 is restricted from being inclined more largely than the allowable angle θ in relation to the first connector 60. With the second connector 80 restricted from being inclined more largely than the allowable angle θ in relation to the first connector 60, the electrical connection between the first connector 60 and the second connector 80 is effectively prevented from being spoiled.

Note that while the guide pins 104 are two cylindrical projections projecting from both sides of the first connector 60 in the present embodiment, this is not restrictive. For example, in an embodiment, the guide pin 104 is a projection that has a polygonal sectional shape and that projects from only one of the holes 103 on both sides of the first connector 60. In this case, the guide hole 106 is formed in a shape for engagement with the guide pin 104. Then, with the guide pin 104 and the guide hole 106 engaged with each other, rotation of the guide hole 106 relative to the guide pin 104, with the projecting direction of the guide pin 104 as a rotational axis, is restricted. The guide pin 104 needs to only be thus configured such that the rotation between the first substrate 71 and the second substrate 85 is restricted when the guide pin 104 is engaged with (connected with) the guide hole 106.

In addition, while the guide hole 106 is a through-hole that penetrates the guide member 105 in the longitudinal direction in the present embodiment, this is not limitative. For example, in place of the guide hole 106, a recess, or hole, recessed from a surface facing to the distal side, of the guide member 105, toward the proximal side may be disposed. In this case, the length of the recess (the depth of the recess) in the longitudinal direction is the fitting length L of fitting to the guide pin 104. Thus, the guide hole 106 needs to only be a recessed hole which can be connected with the guide pin 104.

Figure 11:
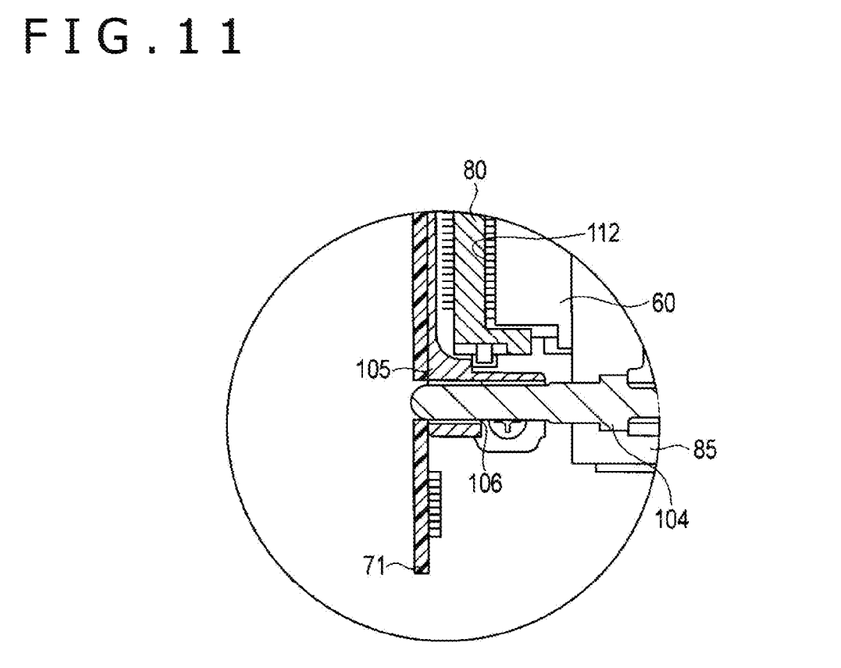
FIG. 11 is an enlarged form, the part indicated by reference symbol 8B of FIG. 8A according to a modification of the embodiment.

Besides, while the first substrate 71 is disposed with the guide pins 104 and the second substrate 85 is disposed with the guide holes 106 in the present embodiment, this is not restrictive. For example, as depicted as a modification in FIG. 11, the first substrate 71 may be disposed with the guide hole 106, and the second substrate 85 may be disposed with the guide pin 104. In this case, the first substrate 71 is provided with the guide member 105, and the guide member 105 is disposed with the second connector 80 and the guide hole 106. Besides, the second substrate 85 is disposed with the first connector 60 to be connected to the second connector 80, and the guide pin 104 fitted to the guide hole 106 is attached.

In addition, while the fitting part 111 of the guide hole 106 of fitting to the guide pin 104 is disposed on the side (proximal side) opposite to the first substrate 71 as compared to that surface (second facing surface 113) of the second connector 80 which faces the first substrate 71 in the present embodiment, this is not limitative. In the case where the fitting part 111 is disposed on the first substrate 71 side as compared to the second facing surface 113, at the time point immediately before insertion of the guide pin 104 into the guide hole 106, a distance is always present between the first facing surface 112 and the second facing surface 113, and the first connector 60 and the second connector 80 are not yet connected together. In other words, a positional relationship similar to that in the present embodiment is obtained.

The connection structure of the substrates used in the present embodiment includes the first substrate (71), the second substrate (85), the first connector (60) disposed on the first substrate (71), the second connector (80) disposed on the second substrate (85) and connected to the first connector (60), the pin (104) disposed on the first substrate (71) and projecting such as to extent from the first substrate (71) along the direction of connection between the first connector (60) and the second connector (80), and the guide member (105) disposed on the second substrate (85) and having the guide hole (106) in which the projection (104) is fitted. The angle (a) is generated between the pin (104) and the guide hole (106) due to the fitting gap between the pin (104) and the guide hole (106) when the pin (104) and the guide hole (106) are fitted to each other. The angle (a) is set to be not greater than the allowable angle (θ) in connection between the first connector (60) and the second connector (80).

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future. The presence of broadening words and phrases such as "one or more," "at least," "but not limited to" or other like phrases in some instances shall not be read to mean that the narrower case is intended or required in instances where such broadening phrases may be absent. Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A substrate connection structure comprising:
    a tubular member having a bottom portion and an opening side;
    a first substrate disposed on either the bottom portion or the opening side in an inside of the tubular member;
    a second substrate disposed on either the bottom portion or the opening side opposite to the first substrate in the inside of the tubular member;
    a first connector disposed on the first substrate;
    a second connector disposed on the second substrate and connected to the first connector;
    a first pin disposed on the first substrate and projecting such as to extend from the first substrate along a direction of connection between the first connector and the second connector; and
    a guide member disposed on the second substrate and having a guide hole in which the first pin is fitted,
    wherein an angle generated between the first pin and the guide hole due to a fitting gap between the first pin and the guide hole when the first pin and the guide hole are fitted to each other is so set as to be not greater than an allowable angle in connection between the first connector and the second connector.

2. The substrate connection structure of claim 1, comprising:
    a first electric circuit disposed on a surface of the first substrate and electrically connected to the first connector; and
    a second electric circuit disposed on a surface of the second substrate and electrically connected to the second connector.

3. The substrate connection structure of claim 1, comprising a second pin that projects from the first substrate along the direction of connection between the first connector and the second connector and that is disposed at such a position that the first connector is interposed between the first pin and the second pin.

4. The substrate connection structure of claim 1, wherein one of the first substrate and the second substrate, the one being disposed on the bottom portion in the inside of the tubular member, is formed in a flat plate shape, and a surface of the substrate disposed on the bottom portion is disposed such as to be substantially parallel to a bottom surface of the tubular member.

5. The substrate connection structure of claim 1, wherein one of the first substrate and the second substrate, the one being disposed on the opening side in the inside of the tubular member, is formed in a flat plate shape, and a surface of the substrate disposed on the opening side is formed in a flat plate shape spreading along a direction substantially orthogonal to a bottom surface of the tubular member.

6. The substrate connection structure of claim 1, wherein the tubular member constitutes an exterior part of a connection portion of an endoscope for connection with an external apparatus.

7. A substrate connection structure comprising:
   a tubular member having a bottom portion and an opening side;
   a first substrate disposed on either the bottom portion or the opening side in an inside of the tubular member;
   a second substrate disposed on either the bottom portion or the opening side opposite to the first substrate in the inside of the tubular member;
   a first connector disposed on the first substrate; a second connector disposed on the second substrate and connected to the first connector;
   a first pin disposed on the first substrate and projecting such as to extend from the first substrate along a direction of connection between the first connector and the second connector; and
   a guide member disposed on the second substrate and having a guide hole in which the first pin is fitted, wherein
   an expression $G/L < \tan \theta$ (theta) is satisfied, where L is a length of a portion of the first pin that is inserted into the guide hole, G is width of a fitting gap between the first pin and the guide hole when the first pin is fitted to guide hole and $\theta$ (theta) is an allowable angle in connection between the first connector and the second connector.

8. The substrate connection structure of claim 7, comprising:
   a first electric circuit disposed on a surface of the first substrate and electrically connected to the first connector; and
   a second electric circuit disposed on a surface of the second substrate and electrically connected to the second connector.

9. The substrate connection structure of claim 7, comprising a second pin that projects from the first substrate along the direction of connection between the first connector and the second connector and that is disposed at such a position that the first connector is interposed between the first pin and the second pin.

10. The substrate connection structure of claim 7, wherein one of the first substrate and the second substrate, the one being disposed on the bottom portion in the inside of the tubular member, is formed in a flat plate shape, and a surface of the substrate disposed on the bottom portion is disposed such as to be substantially parallel to a bottom surface of the tubular member.

11. The substrate connection structure of claim 7, wherein one of the first substrate and the second substrate, the one being disposed on the opening side in the inside of the tubular member, is formed in a flat plate shape, and a surface of the substrate disposed on the opening side is formed in a flat plate shape spreading along a direction substantially orthogonal to the bottom portion of the tubular member.

12. The substrate connection structure of claim 7, wherein the tubular member constitutes an exterior part of a connection portion of an endoscope for connection with an external apparatus.

13. An endoscope comprising:
   an insertion portion;
   an operation portion connected to the insertion portion;
   a universal cable extended from the operation portion; and
   a connection portion disposed at an end portion of the universal cable, the connection portion including a substrate connection structure, the substrate connection structure comprising:
      a tubular member having a bottom portion and an opening side;
      a first substrate disposed on either the bottom portion or the opening side in an inside of the tubular member;
      a second substrate disposed on either the bottom portion or the opening side opposite to the first substrate in the inside of the tubular member;
      a first connector disposed on the first substrate;
      a second connector disposed on the second substrate and connected to the first connector;
      a first pin disposed on the first substrate and projecting such as to extend from the first substrate along a direction of connection between the first connector and the second connector; and
      a guide member disposed on the second substrate and having a guide hole in which the first pin is fitted,
      wherein an angle generated between the first pin and the guide hole due to a fitting gap between the first pin and the guide hole when the first pin and the guide hole are fitted to each other is so set as to be not greater than an allowable angle in connection between the first connector and the second connector.

* * * * *